(12) United States Patent
Cox

(10) Patent No.: US 6,171,334 B1
(45) Date of Patent: Jan. 9, 2001

(54) EXPANDABLE STENT AND METHOD OF USE

(75) Inventor: Daniel L. Cox, Palo Alto, CA (US)

(73) Assignee: Advanced Cardiovascular Systems, Inc., Santa Clara, CA (US)

( * ) Notice: Under 35 U.S.C. 154(b), the term of this patent shall be extended for 0 days.

(21) Appl. No.: 09/099,008

(22) Filed: Jun. 17, 1998

(51) Int. Cl.⁷ ........................................................ A61F 2/06
(52) U.S. Cl. .............................................................. 623/1.15
(58) Field of Search ................................ 623/1, 12, 1.15, 623/1.16, 1.17, 1.18

(56) References Cited

U.S. PATENT DOCUMENTS

| | | |
|---|---|---|
| 3,105,492 | 10/1963 | Jeckel . |
| 3,657,744 | 4/1972 | Ersek . |
| 3,993,078 | 11/1976 | Bergentz et al. . |
| 4,130,904 | 12/1978 | Whalen . |
| 4,140,126 | 2/1979 | Choudhury . |
| 4,159,719 | 7/1979 | Haerr . |
| 4,387,952 | 6/1983 | Slusher . |
| 4,503,569 | 3/1985 | Dotter . |
| 4,504,354 | 3/1985 | George et al. . |
| 4,512,338 | 4/1985 | Balko et al. . |
| 4,531,933 | 7/1985 | Norton et al. . |
| 4,553,545 | 11/1985 | Maass et al. . |
| 4,580,568 | 4/1986 | Gianturco . |
| 4,619,246 | 10/1986 | Molgaard-Nielsen et al. . |
| 4,649,922 | 3/1987 | Wiktor . |
| 4,650,466 | 3/1987 | Luther . |
| 4,655,771 | 4/1987 | Wallsten . |
| 4,681,110 | 7/1987 | Wiktor . |
| 4,706,671 | 11/1987 | Weinrib . |
| 4,733,665 | 3/1988 | Palmaz . |
| 4,739,762 | 4/1988 | Palmaz . |
| 4,740,207 | 4/1988 | Kreamer . |

(List continued on next page.)

FOREIGN PATENT DOCUMENTS

| | | |
|---|---|---|
| 0 221 570 A2 | 5/1987 | (EP) . |
| 0 380 668 | 10/1988 | (EP) . |
| 0 335 341 | 10/1989 | (EP) . |
| 0 338 816 | 10/1989 | (EP) . |
| 0 357 003 A2 | 3/1990 | (EP) . |
| 0 361 192 | 4/1990 | (EP) . |
| 0 364 787 A1 | 4/1990 | (EP) . |

(List continued on next page.)

OTHER PUBLICATIONS

Dotter, Charles T., Transluminally Placed Coilspring Endarterial Tube Grafts, *Investigative Radiology*, pp. 329–332, Sep./Oct. 1969.

Rösch, J., M.D., et al., Transjugular Intrahepatic Portacaval Shunt: An Experimental Work, *The American Journal of Surgery*, pp. 588–592, vol. 121, May 1971.

Dotter, Charles T., Transluminal Expandable Nitinol Coil Stent Grafting: Preliminary Report, *Radiology Journal*, pp. 259–260, Apr. 1983.

Cragg, et al., Non–Surgical Placement of Arterial Endoprostheses: A New Technique Using Nitinol Wire, *Radiology Journal*, pp. 261–263, Apr. 1983.

(List continued on next page.)

Primary Examiner—David H. Willse
Assistant Examiner—Suzette J. Jackson
(74) Attorney, Agent, or Firm—Fulwider Patton Lee & Utecht

(57) ABSTRACT

A configuration for expandable stents wherein a series of circumferentially disposed serpentine elements are spaced such that apexes defined by adjacent serpentine elements are nested within one another and only apexes extending along the same side of each serpentine element are linked. Such configurations impart enhanced coverage areas, expansion ratios and radial strength to the stent.

12 Claims, 4 Drawing Sheets

U.S. PATENT DOCUMENTS

| | | |
|---|---|---|
| 4,762,128 | 8/1988 | Rosenbluth . |
| 4,767,418 | 8/1988 | Deininger . |
| 4,776,337 | 10/1988 | Palmaz . |
| 4,795,458 | 1/1989 | Regan . |
| 4,800,882 | 1/1989 | Gianturco . |
| 4,830,003 | 5/1989 | Wolff et al. . |
| 4,848,343 | 7/1989 | Wallsten et al. . |
| 4,856,516 | 8/1989 | Hillstead . |
| 4,870,966 | 10/1989 | Dellon et al. . |
| 4,877,030 | 10/1989 | Beck et al. . |
| 4,878,906 | 11/1989 | Lindemann et al. . |
| 4,886,062 | 12/1989 | Wiktor . |
| 4,892,539 | 1/1990 | Koch . |
| 4,893,623 | 1/1990 | Rosenbluth . |
| 4,907,336 | 3/1990 | Gianturco . |
| 4,913,141 | 4/1990 | Hillstead . |
| 4,922,905 | 5/1990 | Strecker . |
| 4,943,346 | 7/1990 | Mattelin . |
| 4,950,227 | 8/1990 | Savin et al. . |
| 4,963,022 | 10/1990 | Sommargren . |
| 4,969,458 | 11/1990 | Wiktor . |
| 4,969,890 | 11/1990 | Sugita et al. . |
| 4,986,831 | 1/1991 | King et al. . |
| 4,990,155 | 2/1991 | Wilkoff . |
| 4,994,071 | 2/1991 | MacGregor . |
| 4,998,539 | 3/1991 | Delsanti . |
| 5,002,560 | 3/1991 | Machold et al. . |
| 5,007,926 | 4/1991 | Derbyshire . |
| 5,015,253 | 5/1991 | MacGregor . |
| 5,019,085 | 5/1991 | Hillstead . |
| 5,019,090 | 5/1991 | Pinchuk . |
| 5,026,377 | 6/1991 | Burton et al. . |
| 5,034,001 | 7/1991 | Garrison et al. . |
| 5,035,706 | 7/1991 | Gianturco et al. . |
| 5,037,377 | 8/1991 | Alonso . |
| 5,037,392 | 8/1991 | Hillstead . |
| 5,037,427 | 8/1991 | Harada et al. . |
| 5,041,126 | 8/1991 | Gianturco . |
| 5,059,211 | 10/1991 | Stack et al. . |
| 5,061,275 | 10/1991 | Wallsten et al. . |
| 5,062,829 | 11/1991 | Pryor et al. . |
| 5,064,435 | 11/1991 | Porter . |
| 5,071,407 | 12/1991 | Termin et al. . |
| 5,073,694 | 12/1991 | Tessier et al. . |
| 5,078,720 | 1/1992 | Burton et al. . |
| 5,078,726 | 1/1992 | Kreamer . |
| 5,078,736 | 1/1992 | Behl . |
| 5,084,065 | 1/1992 | Weldon et al. . |
| 5,089,005 | 2/1992 | Harada . |
| 5,089,006 | 2/1992 | Stiles . |
| 5,092,877 | 3/1992 | Pinchuk . |
| 5,100,429 | 3/1992 | Sinofsky et al. . |
| 5,102,417 | 4/1992 | Palmaz . |
| 5,104,404 | 4/1992 | Wolff . |
| 5,108,416 | 4/1992 | Ryan et al. . |
| 5,108,417 | 4/1992 | Sawyer . |
| 5,116,318 | 5/1992 | Hillstead . |
| 5,116,360 | 5/1992 | Pinchuk et al. . |
| 5,116,365 | 5/1992 | Hillstead . |
| 5,122,154 | 6/1992 | Rhodes . |
| 5,123,917 | 6/1992 | Lee . |
| 5,133,732 | 7/1992 | Wiktor . |
| 5,135,536 | 8/1992 | Hillstead . |
| 5,158,548 | 10/1992 | Lau et al. . |
| 5,161,547 | 11/1992 | Tower . |
| 5,163,958 | 11/1992 | Pinchuk . |
| 5,171,262 | 12/1992 | MacGregor . |
| 5,180,368 | 1/1993 | Garrison . |
| 5,183,085 | 2/1993 | Timmermans . |
| 5,192,297 | 3/1993 | Hull . |
| 5,192,307 | 3/1993 | Wall . |
| 5,195,984 | 3/1993 | Schatz . |
| 5,197,978 | 3/1993 | Hess . |
| 5,222,971 | 6/1993 | Willard et al. . |
| 5,226,913 | 7/1993 | Pinchuk . |
| 5,234,456 | 8/1993 | Silverstrini . |
| 5,242,399 | 9/1993 | Lau et al. . |
| 5,242,452 | 9/1993 | Inoue . |
| 5,282,823 | 2/1994 | Schwartz et al. . |
| 5,282,824 | 2/1994 | Gianturco . |
| 5,290,305 | 3/1994 | Inoue . |
| 5,292,331 | 3/1994 | Boneau . |
| 5,304,200 | 4/1994 | Spaulding . |
| 5,314,444 | 5/1994 | Gianturco . |
| 5,314,472 | 5/1994 | Fontaine . |
| 5,330,500 | 7/1994 | Song . |
| 5,344,426 | 9/1994 | Lau et al. . |
| 5,356,433 | 10/1994 | Rowland et al. . |
| 5,421,955 | 6/1995 | Lau et al. . |
| 5,423,885 | 6/1995 | Williams . |
| 5,507,768 | 4/1996 | Lau et al. . |
| 5,514,154 | 5/1996 | Lau et al. . |
| 5,556,413 | 9/1996 | Lam . |
| 5,569,295 | 10/1996 | Lam . |
| 5,575,816 | * 11/1996 | Rudnick et al. ......................... 623/1 |
| 5,591,917 | * 1/1997 | Orth et al. ............................. 623/1 |
| 5,603,721 | 2/1997 | Lau et al. . |
| 5,607,444 | 3/1997 | Lam . |
| 5,649,952 | 7/1997 | Lam . |
| 5,725,549 | 3/1998 | Lam . |
| 5,725,572 | 3/1998 | Lam et al. . |
| 5,728,158 | 3/1998 | Lau et al. . |
| 5,735,893 | * 4/1998 | Lau et al. ............................... 623/1 |
| 5,766,238 | 6/1998 | Lau et al. . |
| 5,782,855 | 7/1998 | Lau et al. . |
| 5,800,526 | * 9/1998 | Anderson et al. ....................... 623/1 |
| 5,843,164 | * 12/1998 | Frantzen et al. ........................ 623/1 |
| 5,843,175 | * 12/1998 | Frantzen ................................. 623/1 |
| 5,868,777 | 2/1999 | Lam . |
| 5,879,381 | * 3/1999 | Moriuchi et al. ........................ 623/1 |
| 5,916,234 | 6/1999 | Lam . |
| 6,066,168 | * 5/2000 | Lau et al. ............................ 623/1.16 |
| 6,066,169 | * 5/2000 | McGuinness ....................... 623/1.16 |

FOREIGN PATENT DOCUMENTS

| | | |
|---|---|---|
| 0 372 789 A3 | 6/1990 | (EP) . |
| 0 407 951 | 1/1991 | (EP) . |
| 0 421 729 A2 | 4/1991 | (EP) . |
| 0 423 916 A1 | 4/1991 | (EP) . |
| 0 428 479 A1 | 5/1991 | (EP) . |
| 0 062 300 | 10/1992 | (EP) . |
| 0 540 290 B1 | 10/1992 | (EP) . |
| 0 517 075 | 12/1992 | (EP) . |
| 0 541 443 A1 | 5/1993 | (EP) . |
| 2 677 872 | 12/1992 | (FR) . |
| 2 070 490 | 9/1981 | (GB) . |
| 2 135 585 | 9/1984 | (GB) . |
| 58-501458 | 9/1983 | (JP) . |
| 62-231657 | 10/1987 | (JP) . |
| 62-235496 | 10/1987 | (JP) . |
| 63-214264 | 9/1988 | (JP) . |
| 64-83685 | 3/1989 | (JP) . |
| 1-299550 | 12/1989 | (JP) . |
| 2-174859 | 7/1990 | (JP) . |
| 2-255157 | 10/1990 | (JP) . |
| 3-9745 | 1/1991 | (JP) . |
| 3-9746 | 1/1991 | (JP) . |
| 3-151983 | 6/1991 | (JP) . |
| 4-25755 | 2/1992 | (JP) . |
| WO 91/07139 | 5/1991 | (WO) . |
| WO 92/06734 | 4/1992 | (WO) . |

WO 92/09246    4/1992   (WO).
WO 97/09945    3/1997   (WO).
WO 97/26840    7/1997   (WO).

OTHER PUBLICATIONS

Maass, et al., Radiological Follow–Up of Transluminally Inserted Vascular Endoprostheses: An Experimental Study Using Expanding Spirals, *Radiology Journal*, pp. 659–663, 1984.

70th Scientific Assembly and Annual Meeting: Scientific Program, *Radiology*, Washington , D.C., Nov. 25–30, 1984, Special Edition, vol. 153(P).

C.R. Bard, PE Plus Peripheral Balloon Dilatation Catheter, *C.R. Bard, Inc.*, Aug. 1985.

Wright, et al., Percutaneous Endovascular Stents: an Experimental Evaluation, *Radiology Journal*, pp. 69–72, 1985.

Duprat, et al., Flexible Balloon–Expanded Stent for Small Vessels, *Radiology Journal*, pp. 276–278, 1987.

Charnsangavej, E., M.D., et al., Endovascular Stent for Use in Aortic Dissection: An In Vitro Experiment, *Radiology*, pp. 323–324, vol. 157, No. 2, Nov. 1985.

Palmaz, et al., Expandable Intraluminal Graft: A Preliminary Study, *Radiology Journal*, pp. 73–77, 1985.

72nd Scientific Assembly and Annual Meeting: RSNA Scientific Program, *Radiology*, Chigago: Nov. 30–Dec. 5, 1986, Special Edition, vol. 161(P).

Program: Day 2 (Nov. 18) The Radiological Society of North America, *Radiology*, Chicago: Nov.30–Dec. 5, 1986, Special Edition, vol. 161(P).

Wallace, Michael J., et al., Tracheobronchial Tree: Expandable Metallic Stents Used in Experimental and Clinical Applications (Work in Progress), *Radiology*, pp. 309–312, vol. 158, Feb. 1986.

Rösch, Josef, M.D., et al., Gianturco Expandable Wire Stents in the Treatment of Superior Vena Cava Syndrome Recurring After Maximum–Tolerance Radiation, *Cancer*, pp. 1243–1246, vol. 60, Sep. 1987.

Yoshioka, Tetsuya, et al., Self–Expanding Endovascular Graft: An Experimental Sutdy in Dogs, *American Journal of Roentgeriology*, pp. 6730676, vol. 151, Oct. 1988.

Rösch, Josef, M.D., et al., Modified Gianturco Expandable Wire Stents in Experimental and Clinical Use, *Annales de Radiologie*, pp. 100–103, vol. 31, No. 2, 1988.

Mirich, David, et al., Percutaneously Placed Endovascular Grafts for Aortic Aneurysms: Feasibility Study, *Radiology*, pp. 1033–1037, 1989 Part 2.

Yoshioka, Tetsuya, et al., Development and Clinical application of Biliary Andoprosthesis Using Expandable Metallic Stents, *Japan Radiological Society*, pp. 1183–1185, vol. 48, No. 9 (with translation).

Anomnatic™ II Positioning Controller, Anorad Corporation, Brochure.

Continuation Application filed Apr. 6, 1998 entitled Expandable Stents and Method for Making Same.

* cited by examiner

EXPANDABLE STENT AND METHOD OF USE

BACKGROUND OF THE INVENTION

The present invention generally relates to intravascular stents and more particularly pertains to improvements thereto that provide for increased coverage and greater expansion ratios without a compromise in strength.

Stents or expandable grafts are implanted in a variety of body lumens in an effort to maintain their patency. These devices are typically intraluminally implanted by use of a catheter which is inserted at an easily accessible location and then advanced to the deployment site. The stent is initially in a radially compressed or collapsed state to enable it to be maneuvered through the lumen. Once in position, the stent is deployed which, depending upon its configuration, is achieved either automatically or actively by the inflation of a balloon about which the stent is carried on the catheter.

As stents are normally employed to hold open an otherwise blocked, constricted or occluded lumen, a stent must exhibit sufficient radial or hoop strength in its expanded state to effectively counter the anticipated forces. Not only is it advantageous to distribute such loads over as much of the stent as possible but it also is most beneficial to distribute the load over as much lumen wall as possible. This will help minimize injury to the vessel wall. Also by minimizing the gaps between stent struts it is possible to prevent prolapse of the plaque between the struts into the lumen. As a consequence, it is desirable to maximize the coverage of the lumen wall by creating uniform, small gaps between the stent struts. It is, however, simultaneously necessary for the stent to be as small and compact as possible in its collapsed state in order to facilitate its advancement through the lumen. As large an expansion ratio as possible is therefore most desirable.

A number of very different approaches have been previously devised in an effort to address these various requirements. A popular approach calls for the stent to be constructed wholly of wire. The wire is bent, woven and/or coiled to define a generally cylindrical structure in a configuration that has the ability to undergo radial expansion. The use of wire has a number of disadvantages associated therewith including for example, a substantially constant cross-section which may cause greater or lesser than an ideal amount of material to be concentrated at certain locations along the stent. Additionally, wire has limitations with respect to the shapes it can be formed into thus limiting the expansion ratio, coverage area and strength that can ultimately be attained therewith. The welding of adjoining sections of wire together has also been previously employed to increase strength albeit with a substantial increase in manufacturing costs.

As an alternative to wire-based structures, stents have been constructed from tube stock. By selectively removing material from such tubular starting material, a desired degree of flexibility and expandability can be imparted to the structure. Chemical etching techniques as well as laser-cutting processes are utilized to remove material from the tube. Laser etching provides for a high degree of precision and accuracy with which very well defined patterns of material can be removed from the tube to conversely leave very precisely and accurately defined patterns of material in tact. The performance parameters of a function of the pattern in which material is removed form the tube stock. The selection of a particular pattern has a profound effect on the coverage area, expansion ratio and strength of the resulting stent.

While the tube-based stents offer many advantages over the wire-based designs, it is nonetheless desirable to improve upon such designs in an effort to further increase coverage area and expansion ratios while maintaining strength.

SUMMARY OF THE INVENTION

The present invention provides for an improved tube-based stent having an increased coverage area, expansion ratio and strength. The improvements arise with the selection of a precisely defined pattern of voids that are cut or etched into the tube stock. The pattern of material that remains to define the stent comprises a series of nested serpentine elements wherein selected apexes are interconnected to one another by bridging members. More particularly, each serpentine element extends circumferentially about the stent such that successive apexes of each element alternatively extend distally and proximally along the stent's surface. Adjacent serpentine elements are spaced about the stent wherein each element is nested in the adjacent elements such that the apexes of one element extend into the space between the apexes of the adjacent element. The serpentine elements are joined to one another along either all of their distal or all of their proximal apexes. Each of a particular element's apexes extending along its interconnected edge is alternatingly joined to the corresponding apexes of proximally and distally adjoining serpentine elements by bridging elements. By properly shaping the junction area between each bridging element and apex, stress risers are reduced or eliminated with a corresponding decrease in the potential for fracturing during expansion. By curving the transverse sections that extend between each of the apexes of a given element, adjacent elements become more tightly packed. Coverage exceeding 20% with expansion ratios of 3.0 are thereby achievable, and expansion ratios exceeding 6.0 are also achievable. More importantly, this dense coverage is uniformly distributed throughout the stent.

These and other features and advantages of the present invention will become apparent from the following detailed description of preferred embodiments which, taken in conjunction with the accompanying drawings, illustrate by way of example the principles of the invention.

DETAILED DESCRIPTION OF THE PREFERRED EMBODIMENTS

The invention is directed to a stent formed from tube stock having a configuration that imparts greater coverage and expansion ratios than have heretofore been possible without compromising strength. Each of the figures illustrates a section of such stents in a flattened plan view for enhanced clarity. Typically the stents of the present invention are formed from tubular members utilizing a chemical etching process or by a laser cutting process. A typical chemical etching process is disclosed in U.S. Pat. No. 5,421,955 (Lau et al.), which is commonly assigned and commonly owned by Advanced Cardiovascular Systems, Inc., which is incorporated herein by reference thereto. Preferably, the stents of the present invention are formed by a laser cutting process which is disclosed in U.S. patent application Ser. No. 08/783,698, which is commonly assigned and commonly owned by Advanced Cardiovascular Systems, Inc., and is incorporated herein by reference thereto.

Figure 1:
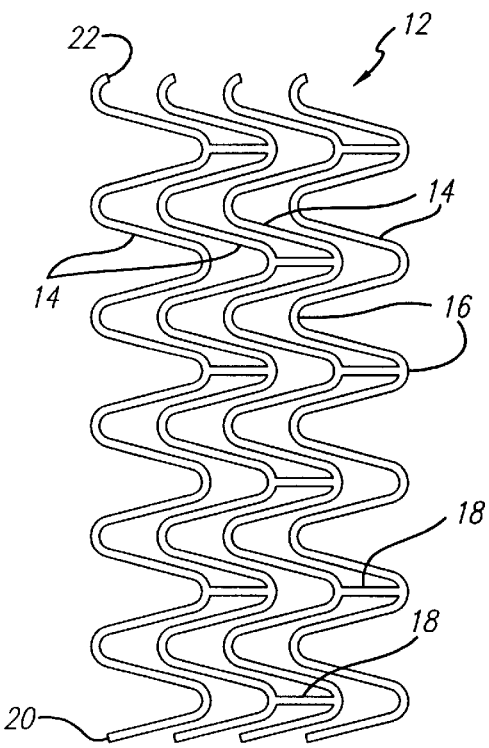
FIG. 1, is a flattened plan view of a section of stent of the present invention in its collapsed state.

FIG. 1 illustrates the general concept of the present invention. Shown is an assembly 12 of serpentine elements 14 wherein apexes 16 of adjacent elements are nested between one another. In its three dimensional form, each serpentine element extends circumferentially about the stent such that for example, end 20 is attached to end 22. The total number of elements assembled in such fashion determine the overall length of the stent. Each of the parallel serpentine elements is joined to the adjacent elements by bridging members 18 that extend from the apexes located along one edge of the serpentine element. Such apexes are alternatingly joined to the corresponding apexes of the proximally and distally adjoining serpentine elements.

Figure 2:
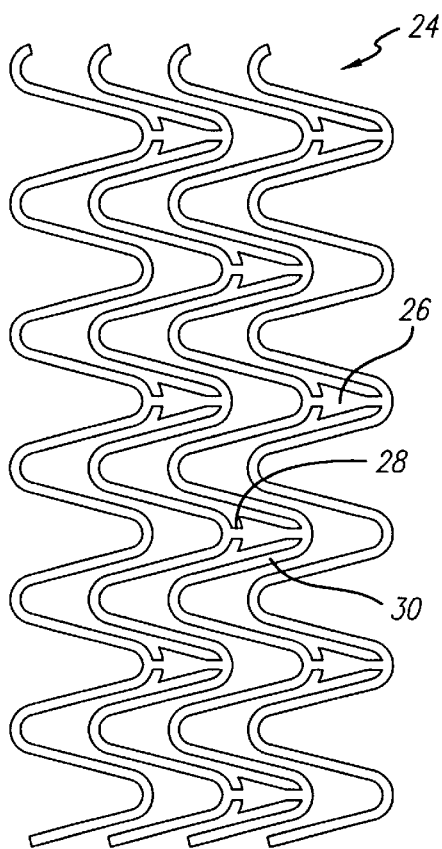
FIG. 2 is a flattened plan view of a section of an alternative embodiment stent in its collapsed state.

FIG. 2 illustrates an alternative embodiment nested design 24 wherein further improvement in terms of coverage area is realized with the modification of the bridging elements 26. Each bridging element is widened to achieve a commensurate increase in surface area. Sufficient clearance 28,30 is maintained between the bridging element and the adjoining sections of the serpentine elements so as to preclude contact and interference during expansion.

Figure 3:
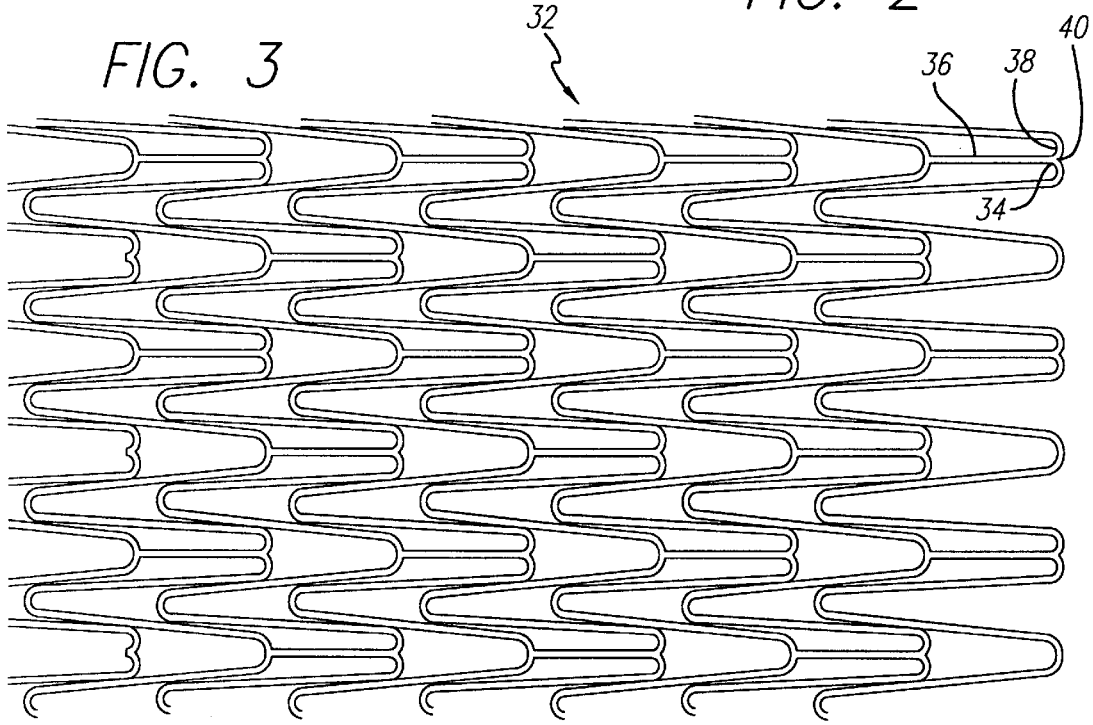
FIG. 3 is flattened plan view of a section of another alternative embodiment stent in its collapsed state.

FIG. 3 illustrates a further alternative embodiment 32 wherein the stresses generated during expansion of the stent near the junction 34 of the bridging element 36 with the concave side 38 of the apex 40 are reduced when compared to the embodiments shown in FIGS. 1 and 2. The configurations shown in FIGS. 1 and 2 define acute angles at such junctures along with an increased concentration of mass at such point. During expansion, the bending of the material would therefore be concentrated adjacent the acute corners and greatly diminished at the center of the apex and thereby promote fractures and the potential for failure. By eliminating the acute angles and the concentration of mass at the apex with its formation into a "W" shape, stress is more evenly distributed along the apex during expansion.

Figure 4:
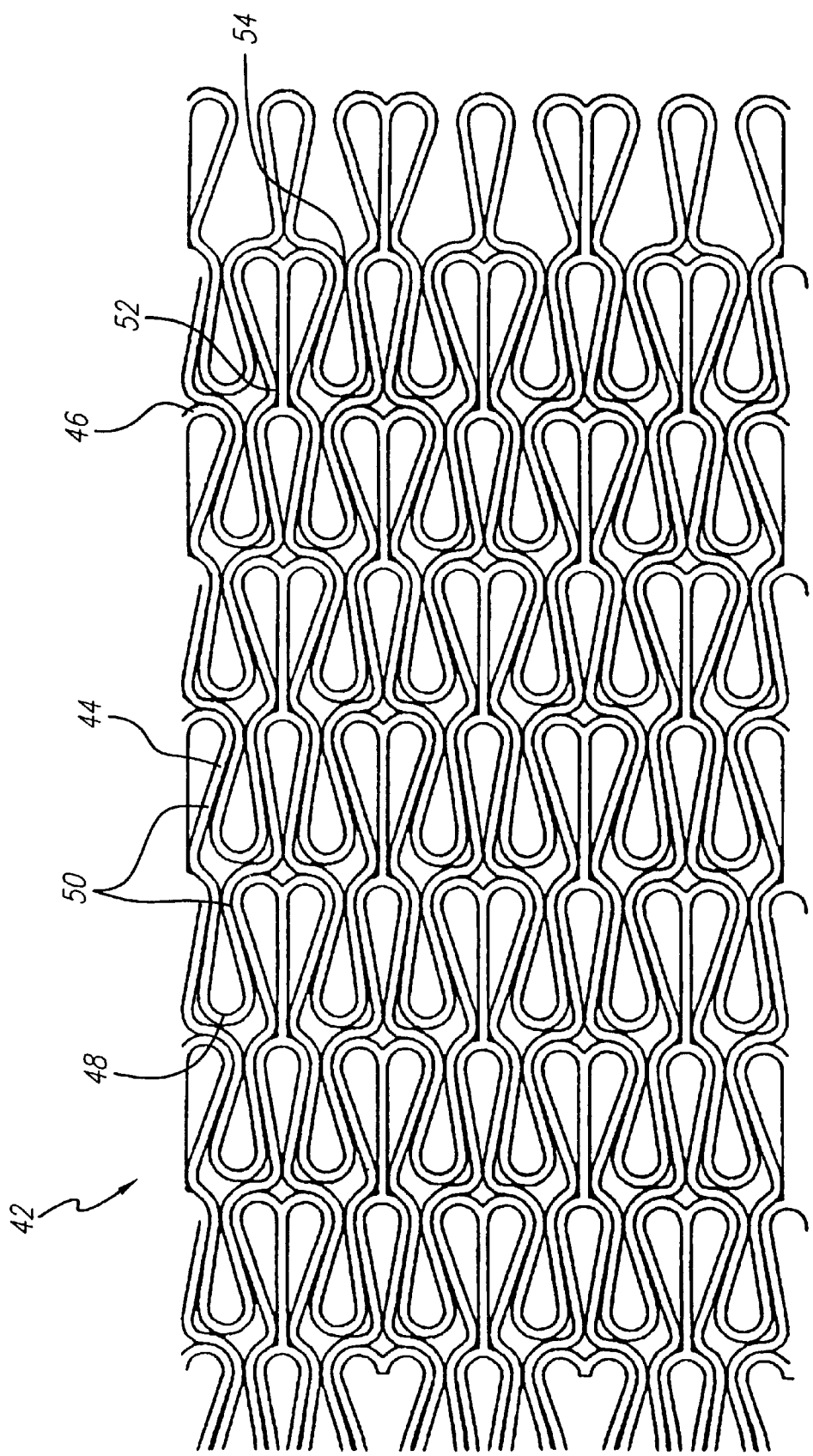
FIG. 4 is flattened plan view of a section of another alternative embodiment stent in its collapsed state.
Figure 5:
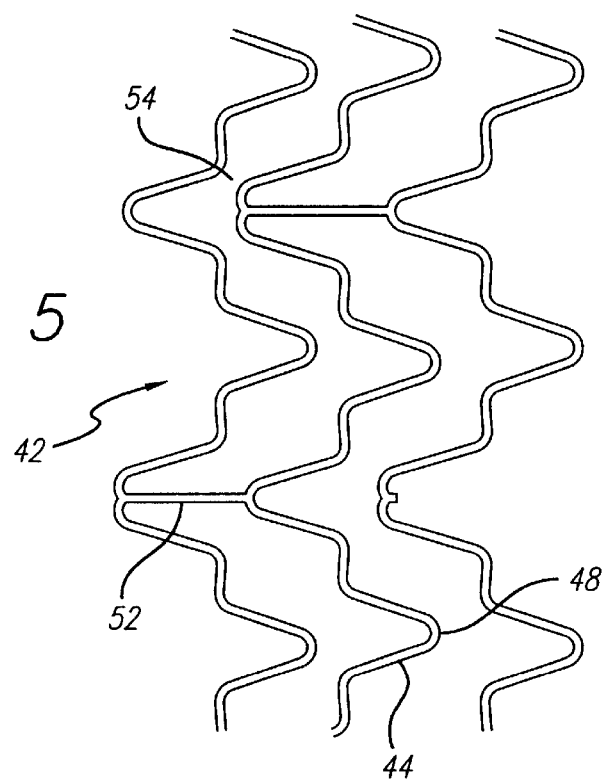
FIG. 5 is view of the stent shown in FIG. 4, in its partially expanded state.
Figure 6:
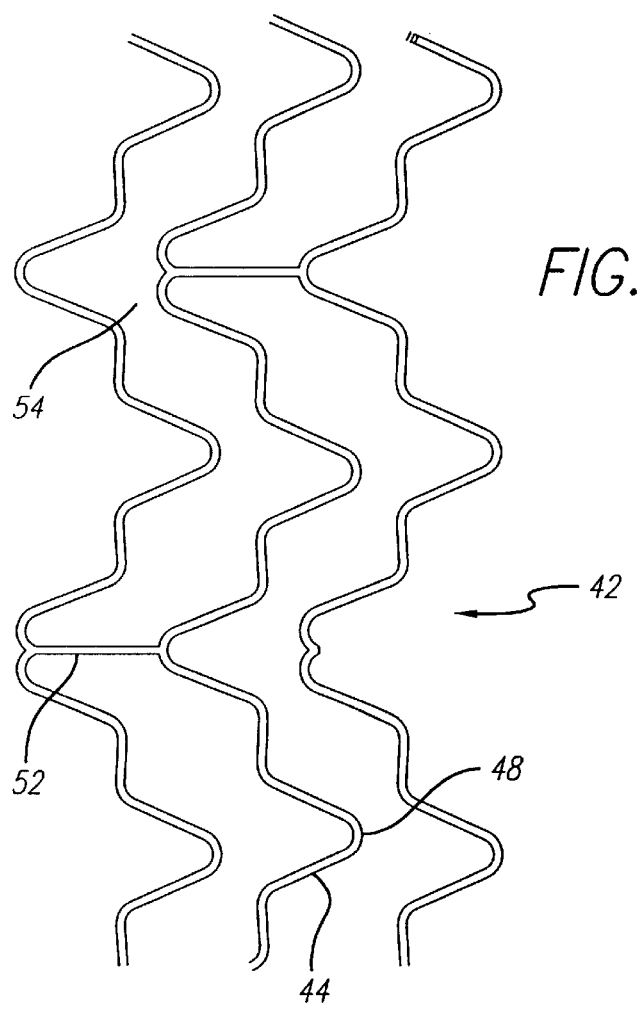
FIG. 6 is view of the stent shown in FIG. 5 in a further expanded state.

FIG. 4 illustrates a further alternative embodiment 42 which incorporates the advantageous features of the embodiment shown in FIG. 3 along with additional features that serve to increase the stent's coverage area as well as its expansion ratio. As is visible in the figure, the transverse section 44 of each serpentine element that links successive apexes 46, 48 is curved at 50 to accommodate the apex of the adjacent serpentine element and to thereby achieve denser packing. The sections are sufficiently curved to come as close as possible to the bridge member at 52 prior to curving around the adjacent apex. Alternating sections are sufficiently curved to substantially close off the apex at 54. The configuration imparts a substantially enhanced coverage area and expansion ratio while nonetheless allowing for the stent to undergo unimpeded expansion. FIG. 5 illustrates such stent configuration partially expanded to show the lack of interference as all elements are caused to move away from one another. FIG. 6 illustrates the stent in a substantially more expanded state. The configuration shown in FIG. 6 yields a theoretical expansion ratio of up to 6.7.

Figure 7:
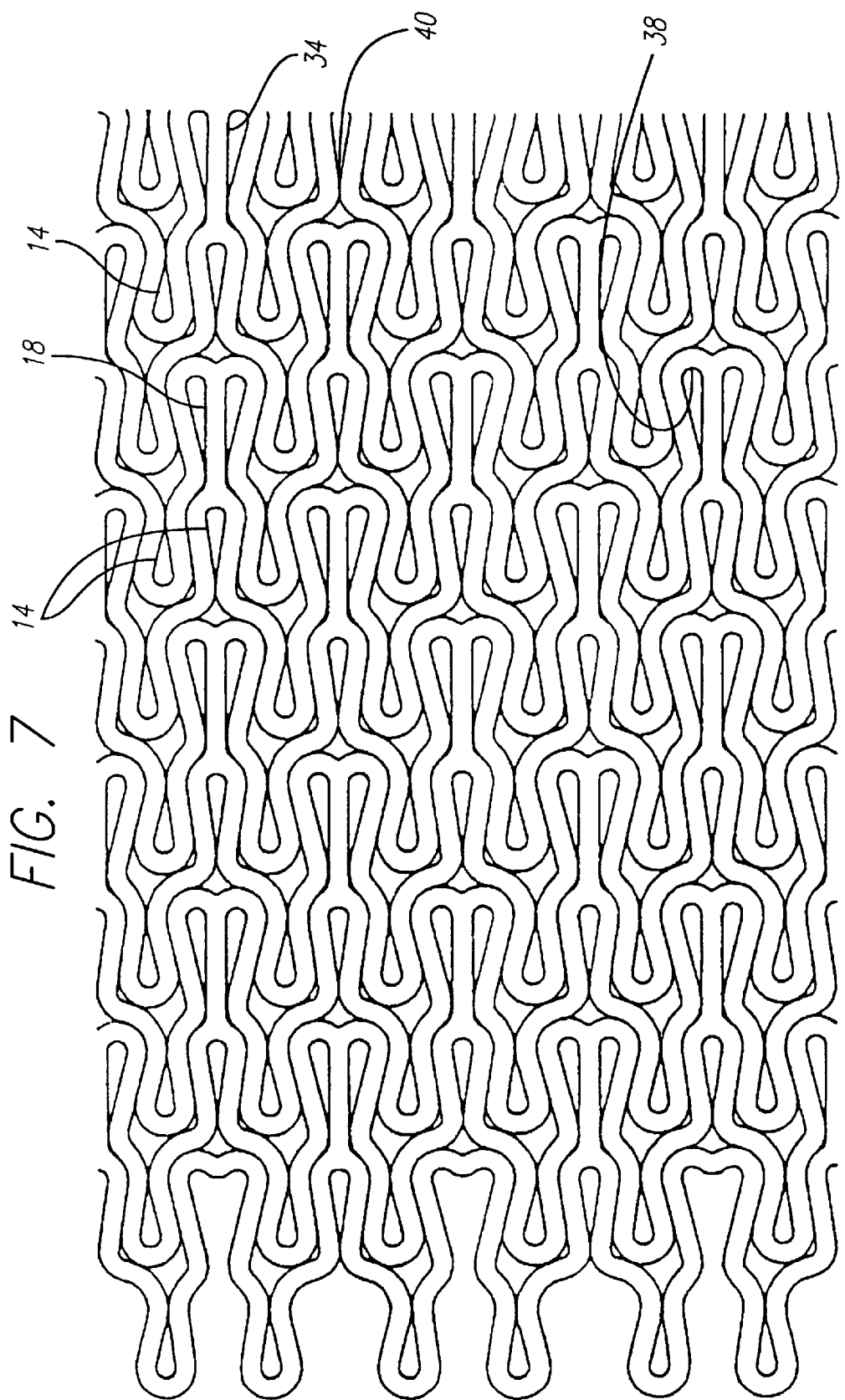
FIG. 7 is a flattened plan view of a section of yet another alternative embodiment stent of the present invention in its collapsed state.

FIG. 7 illustrates the most preferred embodiment of the present invention which incorporates many of the features of the embodiments shown in the other Figures, including the nested configuration of parallel serpentine elements, bridging members joining corresponding apexes of adjacent serpentine elements, the stress-reliefed "W" patterned apex and the curved linking segments. The wider serpentine elements and bridging members along with the tighter radii yield a stent with an exceptionally high coverage area and expansion ratio along with substantial strength.

The stents of the present invention are preferably formed utilizing laser cutting techniques well known in the art. The material used in the manufacture of such stents may be substantially worked stainless steel of low ductility materials such as titanium for balloon expandable versions. Alternatively, NiTi may be used for self expanding embodiments.

While a particular form of the invention has been illustrated and described, it will also be apparent to those skilled in the art that various modifications can be made without departing from the spirit and scope of the invention. The present invention is not limited to stents for any particular body lumen. The size of the stent can vary in terms of inner diameter, outer diameter, wall thickness and length. Accordingly, it is not intended that the invention be limited except by the appended claims.

What is claimed is:

1. A stent comprising:

a series of circumferentially disposed cylindrical rings, each such ring including a series of apexes extending toward a proximal side and a series of apexes extending toward a distal side, wherein apexes of adjacent cylindrical rings are nested within one another and wherein adjacent cylindrical rings are linked by bridging members extending between apexes located on the same side of each ring, the bridging elements extending from a cylindrical ring alternatingly extend between the apexes of the distally and proximally adjoining cylindrical rings; and transverse sections extending between apexes of the cylindrical rings which are sufficiently curved such that transverse sections extending from the same apex substantially contact one another.

2. The stent of claim 1, wherein the bridging elements extend between apexes extending toward the distal side.

3. The stent of claim 1, wherein each distally extending apex that is linked to a distally extending apex of a proximally adjoining cylindrical ring is "W" shaped.

4. The stent of claim 2, wherein the bridging elements extend between apexes extending towards the proximal side.

5. The stent of claim 4, wherein each proximally extending apex that is linked to a proximally extending apex of a distally adjoining cylindrical ring is "W" shaped.

6. The stent of claim 2, wherein the stent is formed from a metal alloy taken from the group of alloys consisting of stainless steel, titanium, tantalum, and nickel titanium.

7. A stent comprising:

a series of circumferentially disposed cylindrical rings, each such ring including a series of apexes extending toward a proximal side and a series of apexes extending toward a distal side, wherein apexes of adjacent cylindrical rings are nested within one another and wherein adjacent cylindrical rings are linked by bridging members extending between apexes located on the same side of each ring, the bridging elements extending from a cylindrical ring alternatingly extend between the apexes of the distally and proximally adjoining cylindrical rings; and transverse sections extending between apexes of cylindrical rings which are sufficiently curved so as to substantially contact bridging elements extending there between.

8. The stent of claim 7, wherein the bridging elements extend between apexes toward the distal side.

9. The stent of claim 8, wherein each distally extending apex that is linked to a distally extending apex of a proximally adjoining cylindrical ring is "W" shaped.

10. The stent of claim 7, wherein the bridging elements extend between apexes extending towards the proximal side.

11. The stent of claim 9, wherein each proximally extending apex that is linked to a proximally extending apex of a distally adjoining cylindrical ring is "W" shaped.

12. The stent of claim 7, wherein the stent is formed from a metal alloy taken from the group of alloys consisting of stainless steel, titanium, tantalum, and nickel titanium.

* * * * *

UNITED STATES PATENT AND TRADEMARK OFFICE
CERTIFICATE OF CORRECTION

PATENT NO. : 6,171,334 B1
DATED : January 9, 2001
INVENTOR(S) : Daniel L. Cox

It is certified that error appears in the above-identified patent and that said Letters Patent is hereby corrected as shown below:

Column 1,
Line 63, after "of" (first occurrence), add --such stents are very much--.

Column 4,
Line 52, claim ,3 change "1", to read --2--.

Signed and Sealed this

Twenty-fourth Day of July, 2001

Attest:

*Nicholas P. Godici*

NICHOLAS P. GODICI
*Attesting Officer*   *Acting Director of the United States Patent and Trademark Office*

UNITED STATES PATENT AND TRADEMARK OFFICE
CERTIFICATE OF CORRECTION

PATENT NO.     : 6,171,334 B1
DATED          : January 9, 2001
INVENTOR(S)    : Daniel L. Cox It is certified that error appears in the above-identified patent and that said Letters Patent is hereby corrected as shown below:

<u>Column 4,</u>
Line 55, change "2", to read -- 1 --.

Signed and Sealed this

Twenty-third Day of March, 2004

JON W. DUDAS
*Acting Director of the United States Patent and Trademark Office*